United States Patent
Villas-Boas

(10) Patent No.: US 9,255,109 B2
(45) Date of Patent: Feb. 9, 2016

(54) FUNGICIDAL COMPOUNDS AND METHODS OF THEIR USE

(75) Inventor: Silas Granato Villas-Boas, Auckland (NZ)

(73) Assignee: Auckland Uniservices Limited, Auckland (NZ)

(*) Notice: Subject to any disclaimer, the term of this patent is extended or adjusted under 35 U.S.C. 154(b) by 570 days.

(21) Appl. No.: 13/514,867

(22) PCT Filed: Dec. 9, 2010

(86) PCT No.: PCT/NZ2010/000249
§ 371 (c)(1), (2), (4) Date: Aug. 20, 2012

(87) PCT Pub. No.: WO2011/071396
PCT Pub. Date: Jun. 16, 2011

(65) Prior Publication Data
US 2013/0078272 A1    Mar. 28, 2013

(30) Foreign Application Priority Data

Dec. 9, 2009 (NZ) ........................ 581846
Apr. 16, 2010 (NZ) ........................ 584694

(51) Int. Cl.
| | |
|---|---|
| *C12P 1/02* | (2006.01) |
| *A01N 65/00* | (2009.01) |
| *A61K 36/06* | (2006.01) |
| *A61K 36/09* | (2006.01) |
| *A01H 15/00* | (2006.01) |
| *C07D 493/08* | (2006.01) |
| *C12P 17/18* | (2006.01) |
| *C12R 1/645* | (2006.01) |
| *A61K 31/357* | (2006.01) |
| *A61K 36/062* | (2006.01) |

(52) U.S. Cl.
CPC ............ *C07D 493/08* (2013.01); *A61K 31/357* (2013.01); *A61K 36/06* (2013.01); *A61K 36/062* (2013.01); *C12P 17/181* (2013.01); *C12R 1/645* (2013.01)

(58) Field of Classification Search
None
See application file for complete search history.

(56) References Cited

FOREIGN PATENT DOCUMENTS

| | | |
|---|---|---|
| JP | H3-14588 | 1/1991 |
| JP | 3227991 | 10/1991 |
| JP | 3227991 A | 10/1991 |
| JP | 2001-78758 | 3/2001 |
| JP | 2002-47281 | 2/2002 |
| WO | 98/31824 | 7/1998 |
| ZA | 199306171 A | 10/1994 |

OTHER PUBLICATIONS

Lee et al. Bull. Korean Chem. Soc. 2007, vol. 28, No. 5 pp. 877-879.*
Zhou et al. Plant Disease,vol. 73 No. 8: pp. 639-642, 1989.*
Pieckenstain et al. Mycol. Res. 105 (1) : pp. 77-84, 2001.*
Riungu et al. Plant Pathology Journal 7 (1): 13-19, 2008.*
Wittig. Effect of Resident Epiphytic Fungi on Development of Brown Rot Blossom Blight of Stone Fruits. Masters Thesis, 1992.*
Organ et al. (2000) "Approach toward the total synthesis of orevactaene. Part 1: Assembly of the contiguous trisubstituted olefin component," Tetrahedron Letters 41:6945-6949.
Shu et al. (1997) "Orevactaene, a novel binding inhibitor of HIV-1 Rev protein to Rev response element (RRE) from Epicoccum nigrum WC47880," Bioorganic & Medicinal Chemistry Letters 7(17): 2295-2298.
Tripathi et al. (2004) "Exploitation of natural products as an alternative strategy to control postharvest fungal rotting of fruit and vegetable," Postharvest Biol. Technol. 32: 235-245.
Verduyn et al. (1992) "Effect of benzoic acid on metabolic fluxes in yeasts: A continuous-culture steady on regulation of respiration and alcoholic fermentation," Yeast 8: 501-517.
Arenal et al. (1999) "Evaluation of different PCR-based DNA fingerprinting techniques for assessing the genetic variability of isolates of the fungus Epicoccum nigrum", Journal of Applied Microbiology vol. 87: 898-906.
Arenal et al. (2002) "Comparison of genotypic and phenotypic techniques for assessing the variability of the fungus Epicoccum nigrum", Journal of Applied Microbiology vol. 93: 36-45.
Brown et al. (1987) "Antifungal compounds produced by Epicoccum purpurascens against soil-borne plant pathogenic fungi", Soil Biol. Biochem. vol. 19(6): 657-664.
Favaro et al. (2011) "Polyphasic Analysis of Intraspecific Diversity in Epicoccum nigrum Warrants Reclassification into Separate Species", PLoS ONE vol. 6(8): e14828.
Frederick et al. (1981) "Production and Isolation of Siderophores from the Soil Fungus Epicoccum purpurascens", Biochemistry vol. 20: 2432-2436.
Mielnichuk et al. (2007) "Interaction between Epicoccum purpurascens and xylophagous basidiomycetes on wood blocks", Forest Pathology vol. 37: 236-242.
Pažoutová et al. (2002) "Relationship of Cerebella to Epicoccum and their closest relatives among Dothideales", Czech. Mycol. 53 (4): 155-160.

\* cited by examiner

Primary Examiner — Chris R Tate
Assistant Examiner — Douglas F White
(74) Attorney, Agent, or Firm — Lathrop & Gage LLP

(57) ABSTRACT

Antifungal compounds, an antifungal compound extracted from *Epicoccum purpurascens*, also known as *Epicoccum nigrum*, methods of producing the antifungal compounds, isolates and compositions comprising the antifungal compounds, and methods of using the antifungal compounds.

5 Claims, No Drawings

FUNGICIDAL COMPOUNDS AND METHODS OF THEIR USE

CROSS-REFERENCE TO RELATED APPLICATIONS

This application is a U.S. National Stage Application filed under 35 U.S.C. §371 of International Application No. PCT/NZ2010/000249, filed Dec. 9, 2010, which claims the benefit of New Zealand Application No. 584694, filed Apr. 16, 2010, and New Zealand Application No. 581846, filed Dec. 9, 2009. All three of these applications are hereby incorporated by reference in their entireties.

FIELD OF THE INVENTION

The present invention relates to antifungal compounds, an antifungal compound extracted from *Epicoccum purpurascens*, also known as *Epicoccum nigrum*. The invention also relates to methods of producing the antifungal compounds, isolates and compositions comprising the antifungal compounds, and methods of using the antifungal compounds.

BACKGROUND

Synthetic fungicides have been used as the main tool to control fungal infection on growing and harvested crops. It has been estimated that over 23 million kilograms of these synthetic fungicides are used annually worldwide and it is felt that production and marketing of fruit and vegetables would not be possible without their use (Tripathi and Dubey, 2004).

The use of such chemicals has increased consumer concern and their use is becoming more and more restricted due to toxicity problems and environmental pollution. This there is an increasing interest in finding useful alternatives to chemical fungicides that are safe and have negligible risk to human health and the environment.

Among these strategies, natural products with antifungal activity are attractive because they are readily biodegradable and, therefore, could be less toxic to the environment and consumers.

Therefore it is an object of the present invention to provide an improved or alternative antifungal compound or to at least provide the public with a useful choice.

SUMMARY OF THE INVENTION

Accordingly, in a first aspect the invention relates to an isolated or substantially pure compound of Formula (I) or a salt, solvate, or hydrate thereof

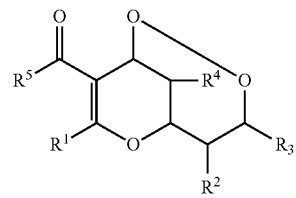

(I)

wherein $R^1$ is hydrogen, hydroxyl, or a $C_1$ to $C_{30}$ alkyl or alkoxy group optionally comprising one or more double bonds, optionally comprising one or more triple bonds, and optionally substituted with one or more groups selected from hydroxyl, halogen, cyano, nitro, amino, alkylamino, dialkylamino, alkyl, alkoxy, alkylthio, haloalkyl, —$NR_aR_b$, —$NR_aC(\!=\!O)R_b$, —$NR_aC(\!=\!O)NR_aR_b$, —$NR_aC(\!=\!O)OR_b$, —$NR_aSO_2R_b$, $OR_a$, —$C(\!=\!O)R_a$, —$C(\!=\!O)OR_a$, —$C(\!=\!O)NR_aR_b$, —$OC(\!=\!O)NR_aR_b$, —SH, —$SR_a$, —$SOR_a$, —$S(\!=\!O)_2R_a$, —$OS(\!=\!O)_2R_a$, —$S(\!=\!O)_2OR_a$, wherein $R_a$ and $R_b$ are the same or different and independently selected from the group comprising hydrogen, halogen, alkyl, haloalkyl, thioalkyl, and substituted alkyl; and $R^2$, $R^3$, $R^4$ and $R^5$ are independently selected from hydrogen, alkyl, substituted alkyl, alkenyl, substituted alkenyl, alkynyl, substituted alkynyl, alkoxy, substituted alkoxy, alkylthio, substituted alkylthio, haloalkyl, substituted haloalkyl, hydroxyl, halogen, cyano, nitro, amino, alkylamino, dialkylamino, —$NR_aR_b$, —$NR_aC(\!=\!O)R_b$, —$NR_aC(\!=\!O)NR_aR_b$, —$NR_aC(\!=\!O)OR_b$, —$NR_aSO_2R_b$, $OR_a$, —$C(\!=\!O)R_a$, —$C(\!=\!O)OR_a$, —$C(\!=\!O)NR_aR_b$, —$OC(\!=\!O)NR_aR_b$, —SH, —$SR_a$, —$SOR_a$, —$S(\!=\!O)_2R_a$, —$OS(\!=\!O)_2R_a$, —$S(\!=\!O)_2OR_a$, wherein $R_a$ and $R_b$ are the same or different and independently selected from the group comprising hydrogen, halogen, alkyl, haloalkyl, thioalkyl, and substituted alkyl.

In a second aspect the invention relates to an isolate obtained or obtainable from *Epicoccum purpurascens* comprising at least about 1 to 99% by weight of a compound of Formula (I) or a salt thereof.

In a third aspect the invention relates to a composition comprising a compound of Formula (I) or a salt, solvate, or hydrate thereof or an isolate obtained or obtainable from *Epicoccum purpurascens* comprising at least about 1 to 99% by weight of a compound of Formula (I) or a salt thereof and an agriculturally or pharmaceutically acceptable carrier.

In a fourth aspect the invention relates to a method of treating or preventing a fungal infection comprising administration of a compound or isolate of the invention to a subject in need thereof.

In a fifth aspect the invention relates to a method of treating or preventing a fungal infection comprising application of a compound or isolate of the invention to a target surface in need thereof, such as a plant or its surroundings.

In a sixth aspect the invention relates to a method of producing a compound of Formula (IV) or a salt thereof

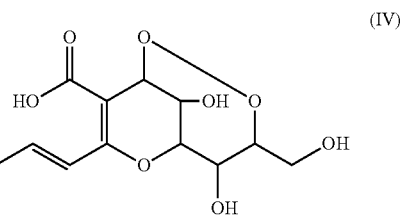

(IV)

the method comprising
(a) culturing an organism of the genus *Epicoccum*, preferably *Epicoccum purpurascens* in a culture medium to produce the compound of Formula (IV) or salt thereof, and
(b) optionally extracting the compound of Formula (IV) or salt thereof from the culture medium.

In a seventh aspect the invention relates to a biologically pure culture of *Epicoccum purpurascens* strain SVB-F1 on deposit at the National Measurement Institute, Australia (NMI) under accession number V10/000331, deposited 18 Mar. 2010, or a culture having the identifying characteristics thereof.

In an eighth aspect the invention relates to a method of treating or preventing a fungal infection comprising administering *Epicoccum purpurascens* strain SVB-F1 or a culture having identifying characteristics thereof or a composition comprising *Epicoccum purpurascens* strain SVB-F1 or a culture having the identifying characteristics thereof to a subject in need thereof.

In a ninth aspect, the invention relates to a method of treating or preventing a fungal infection comprising applying *Epicoccum purpurascens* strain SVB-F1 or a culture having the identifying characteristics thereof or a composition comprising *Epicoccum purpurascens* strain SVB-F1 or a culture having the identifying characteristics thereof to a target surface in need thereof.

The following embodiments may relate to any of the above aspects.

In one embodiment of a compound of Formula (I), $R^1$ is selected from or is substituted with alkylcarbonylalkyl, alkylcarbonyloxyalkyl, alkyloxyalkyl, alkylsulfonyl, alkylsulfinyl, alkylthioalkyl, hydroxyalkyl, mono- or di(alkyl)aminoalkyl.

In one embodiment of a compound of Formula (I), $R^1$ is hydrogen, hydroxyl, or a $C_1$ to $C_{30}$ alkyl or alkoxy group optionally comprising one or more double bonds, and optionally substituted with one- or more groups selected from lower alkyl, lower alkenyl, lower alkoxy, hydroxyl and carboxyl.

In one embodiment of a compound of Formula (I), $R^1$ is a $C_1$ to $C_{30}$ alkyl or alkoxy group comprising one or more double bonds, and substituted with one or more groups selected from lower alkyl, lower alkenyl, lower alkoxy, hydroxyl and carboxyl.

In one embodiment of a compound of Formula (I), $R^2$, $R^3$, $R^4$, and $R^5$ are independently selected from hydrogen, alkyl, substituted alkyl, alkoxy, substituted alkoxy, hydroxyl, and halogen, or are independently selected from hydrogen, methyl, methoxy and hydroxyl. In another embodiment of a compound of Formula (I), $R^2$, $R^3$, $R^4$, and $R^5$ are independently selected from hydrogen and hydroxyl.

In one embodiment the compound of Formula I comprises a compound of Formula (II)

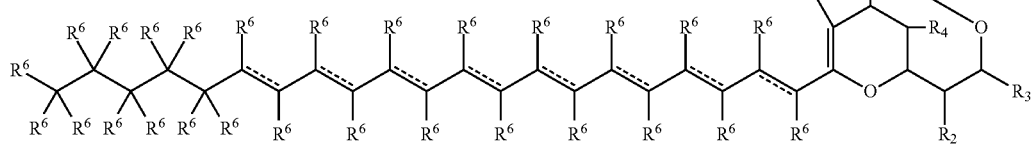

(II)

wherein
$R^2$, $R^3$, $R^4$, and $R^5$ are as defined above;
each ------ is independently a single bond, a double bond or a triple bond; and
each $R^6$ is independently selected from hydrogen, hydroxyl, halogen, cyano, nitro, amino, alkylamino, dialkylamino, alkyl, alkoxy, alkylthio, haloalkyl, —$NR_aR_b$, —$NR_aC(=O)R_b$, —$NR_aC(=O)NR_aR_b$, —$NR_aC(=O)OR_b$, —$NR_aSO_2R_b$, $OR_a$, —$C(=O)R_a$, —$C(=O)OR_a$, —$C(=O)NR_aR_b$, —$OC(=O)NR_aR_b$, —SH, —$SR_a$, —$SOR_a$, —$S(=O)_2R_a$, —$OS(=O)_2R_a$, —$S(=O)_2OR_a$, wherein $R_a$ and $R_b$ are the same or different and independently selected from the group comprising hydrogen, halogen, alkyl, haloalkyl, thioalkyl, and substituted alkyl.

In one embodiment of a compound of Formula (II), each ------ is independently a single bond or a double bond (cis or trans), or each ------ is a double bond. In one embodiment of a compound of Formula (II), $R^2$, $R^3$, $R^4$, and $R^5$ are independently selected from hydrogen, alkyl, substituted alkyl, alkoxy, substituted alkoxy, hydroxyl, and halogen, or are independently selected from hydrogen, methyl, methoxy and hydroxyl. In another embodiment of a compound of Formula (II), $R^2$, $R^3$, $R^4$, and $R^5$ are independently selected from hydrogen and hydroxyl. In one embodiment of a compound of Formula (II), each $R^6$ is independently selected from hydrogen, methyl, methoxy, hydroxyl and carboxyl. In another embodiment of a compound of Formula (II), each $R^6$ is independently selected from hydrogen, methyl, and carboxyl.

In another embodiment the compound of Formula I comprises a compound of Formula (III)

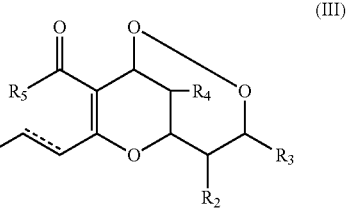

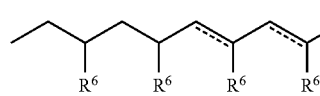

(III)

wherein $R^2$, $R^3$, $R^4$, and $R^5$ are as defined above;

each ----- is independently a single bond, a double bond or a triple bond; and each $R^6$ is independently selected from hydroxyl, halogen, cyano, nitro, amino, alkylamino, dialkylamino, alkyl, alkoxy, alkylthio, haloalkyl, —$NR_aR_b$, —$NR_aC(=O)R_b$, —$NR_aC(=O)NR_aR_b$, —$NR_aC(=O)OR_b$, —$NR_aSO_2R_b$, $OR_a$, —C(=O)$R_a$, —C(=O)O$R_a$, —C(=O)N$R_aR_b$, —OC(=O)N$R_aR_b$, —SH, —S$R_a$, —SO$R_a$, —S(=O)$_2R_a$, —OS(=O)$_2R_a$, —S(=O)$_2$O$R_a$, wherein $R_a$ and $R_b$ are the same or different and independently selected from the group comprising hydrogen, halogen, alkyl, haloalkyl, thioalkyl, and substituted alkyl.

In one embodiment of a compound of Formula (III), each ----- is independently a single bond or a double bond (cis or trans), or each ----- is a double bond. In one embodiment of a compound of Formula (III), $R^2$, $R^3$, $R^4$, and $R^5$ are independently selected from hydrogen, alkyl, substituted alkyl, alkoxy, substituted alkoxy, hydroxyl, and halogen, or are independently selected from hydrogen, methyl, methoxy and hydroxyl. In another embodiment of a compound of Formula (III), $R^2$, $R^3$, $R^4$, and $R^5$ are independently selected from hydrogen and hydroxyl. In one embodiment of a compound of Formula (III), each $R^6$ is independently selected from hydrogen, methyl, methoxy, hydroxyl and carboxyl. In another embodiment of a compound of Formula (III), each $R^6$ is independently selected from hydrogen, methyl, and carboxyl.

In one embodiment the compound of Formula I comprises a compound of Formula (IIIA)

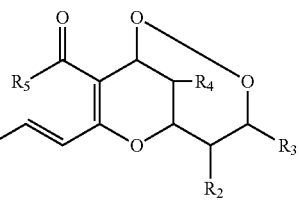

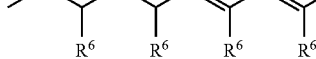

(IIIA)

wherein $R^2$, $R^3$, $R^4$, and $R^5$ are independently selected from hydrogen, methyl, methoxy and hydroxyl; and each $R^6$ is independently selected from hydrogen, methyl, methoxy, hydroxyl and carboxyl.

In yet another embodiment the compound of Formula I comprises a compound of Formula (IV)

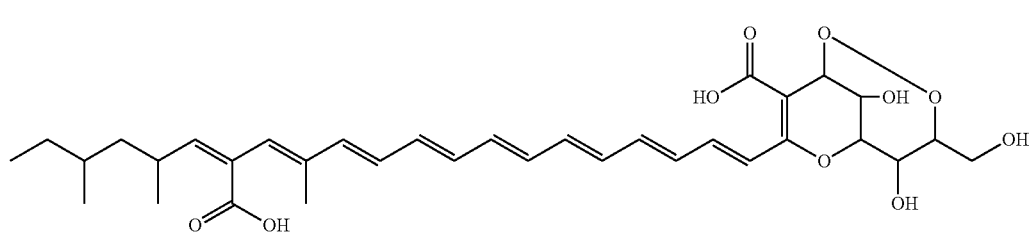

(IV)

In one embodiment the compound of Formula (I) to (IV) is obtained or obtainable from an organism of the genus *Epicoccum*. In another embodiment the compound of Formula (I) to (IV) is obtained or obtainable from *Epicoccum purpurascens*. In another embodiment the compound of Formula (I) to (IV) is obtained or obtainable from *Epicoccum purpurascens* strains SVB-F1 (V10/000331), ICMP2048, ICMP2931, ICMP10458, ICMP10459, ICMP10460, ICMP11503, ICMP15700, ICMP15816 or ICMP16305.

In one embodiment the fungus comprises a filamentous fungus and the fungal infection comprises a filamentous fungal infection.

In another embodiment the fungus comprises a filamentous fungus that is an animal pathogen and the fungal infection comprises a filamentous fungal infection of animals.

In yet another embodiment the fungus comprises a phytopathogenic filamentous fungus and the fungal infection comprises a phytopathogenic filamentous fungal infection.

In one embodiment the fungus is of the family Gnomoniaceae (for example, *Apiognomonia supraseptata*), Cortiaceae (for example, *Rhizoctonia solani*), Magnoporthaceae (for example, *Magnaporthe grisea*), Mycosphaerellaceae, Pleosporaceae (for example, *Alternaria alternata*), Sclerotiniaceae (for example, *Botrytis cinerea* or *Sclerotinia sclerotiorum*), Typhulaceae (for example, *Sclerotium cepivorumi*), Valsaceae (for example, *Phomopsis viticola*), or Venturiaceae (for example, *Venturia inaequalis*).

In another embodiment the fungus is of the genus *Apiognomonia* (for example, *Apiognomonia supraseptata*), *Alternaria* (for example, *Alternaria alternata*), *Botrytis* (for example, *Botrytis cinerea*), *Botryotinia*, *Magnaporthe* (for example, *Magnaporthe grisea*), *Phomopsis* (for example, *Phomopsis viticola*), *Rhizoctonia* (for example, *Rhizoctonia solani*), *Sclerotinia* (for example, *Sclerotinia scleronorum*), *Sclerotium* (for example, *Sclerotium cepivorumi*), or Venturiaceae (for example, *Venturia inaequalis*).

In yet another embodiment the fungus is *Apiognomonia supraseptata*, *Alternaria alternata*, *Botrytis cinerea*, *Botryotinia* spp., *Magnaporthe grisea*, *Phomopsis viticola*, *Rhizoctonia solani*, *Sclerotinia sclerotiorum*, *Sclerotium cepivorumi*, or *Venturia inaequalis*.

In one embodiment the fungal infection is selected from anthracnose (for example, oak anthracnose), canker (for example, stem canker of tomato), ringspot disease (for example, ringspot disease of pear), blight and lesions of vegetables (for example, parsley leaf blight), fruit rot (for example, grey rot and noble rot of grapes), blast disease or bright disease (for example, rice rotten neck, rice seedling blight, blast of rice, oval leaf spot of graminea, pitting disease, ryegrass blast, and johnson spot), cane and leaf spot (for example, leaf and berry spot of grapes), damping off (for example, death of seedlings in agriculture), wire stem (for example, disease of cabbage, cauliflower and related plants), white mould (for example, white mould in soy beans and dry edible beans), wilt or stalk rot (for example, steam rot in canola), southern blight (blight of wheat and tomato), and scab lesions (for example, apple scab).

In one embodiment the fungus is of the family Dothioraceae (for example, *Hortaea werneckii*, syn. *Phaeoannellomyces werneckii*), Trichosporonaceae (for example, *Trichosporon beigelii*), Piedraiaceae (for example, *Piedraia hortae*), Arthrodermataceae (for example, *Trichophyton rubrum*, *Microsporum gypseum* or *Epidermophyton floccosum*), Sphaeropsidaceae (for example, *Scytalidium dimidiatum*, syn *Hendersonula toruloidea* or *Scytalidium hyalinum*), or Microascaceae (for example, *Scopulariopsis brevicaulis*).

In one embodiment the fungus is of the genus *Hortaea* (for example, *Hortaea werneckii*, syn. *Phaeoannellomyces werneckii*), *Trichosporon* (for example, *Trichosporon beigelii*, *Piedraia* (for example, *Piedraia hortae*), *Trichophyton* (for example, *Trichophyton rubrum*), *Microsporum* (for example, *Microsporum gypseum*), *Epidermophyton* (for example, *Epidermophyton floccosum*), *Hendersonula* (for example, *Hendersonula toruloidea*), *Scytalidium* (for example, *Scytalidium hyalium*), or *Scopulariopsis* (for example, *Scopulariopsis brevicaulis*).

In one embodiment the isolate obtained or obtainable from *Epicoccum purpurascens* comprises at least about 1, 2, 3, 4, 5, 6, 7, 8, 9, 10, 15, 20, 25, 30, 35, 40, 45, 50, 55, 60, 65, 70, 75, 80, 85, 90, 95 or 99% by weight of a compound of Formula (I) or a salt thereof, and useful ranges may be selected between any of these values (for example, about 1 to about 99, about 5 to about 99, about 10 to about 99, about 15 to about 99, about 20 to about 99, about 25 to about 99, about 30 to about 99, about 35 to about 99, about 40 to about 99, about 45 to about 99, about 50 to about 99, about 55 to about 99, about 60 to about 99, about 65 to about 99, about 70 to about 99, about 75 to about 99, about 80 to about 99, about 85 to about 99, or about 90 to about 99% by weight).

It should be understood that any isolates useful herein include isolates obtained or obtainable from a culture comprising *Epicoccum purpurascens* or a culture from which *Epicoccum purpurascens* has been removed.

In one embodiment the method of treating or preventing the fungal infection comprises preventing or decreasing fungal growth or preventing or decreasing spore germination or both.

In one embodiment a composition useful herein comprises at least about, 0.001, 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 mg/mL of a compound of Formula (I) to (IV), preferably a compound of Formula (IV), and useful ranges may be selected between any of these values (for example, about 0.01 to about 1.0, about 0.01 to about 10, about 0.01 to about 20, about 0.01 to about 30, about 0.01 to about 40, about 0.01 to about 50, about 0.01 to about 60, about 0.01 to about 70, about 0.01 to about 80, about 0.01 to about 90, about 0.01 to about 100, about 0.1 to about 1.0, about 0.1 to about 10, about 0.1 to about 20, about 0.1 to about 30, about 0.1 to about 40, about 0.1 to about 50, about 0.1 to about 60, about 0.1 to about 70, about 0.1 to about 80, about 0.1 to about 90, about 0.1 to about 100, about 0.7 to about 1.0, about 0.7 to about 10, about 0.7 to about 20, about 0.7 to about 30, about 0.7 to about 40, about 0.7 to about 50, about 0.7 to about 60, about 0.7 to about 70, about 0.7 to about 80, about 0.7 to about 90, or about 0.7 to about 100 mg/mL).

In various embodiments the composition useful herein comprises a reproductively viable form and amount of *Epicoccum purpurascens* SVB-F1.

In one embodiment, the composition comprises a reproductively viable form and amount of *Epicoccum purpurascens* SVB-F1 and one or more compounds or isolates of the invention.

In one embodiment a composition useful herein may comprise one or more additional agricultural agents. In another embodiment a method of the invention may comprise separate, simultaneous or sequential administration of the compound of Formula (I) to (IV) or the isolate and one or more additional agricultural agents. In one embodiment the additional agricultural agent is selected from one or more fungicides, one or more fertilizers, one or more antibiotics, one or more antivirals or one or more insecticides. In one embodiment the compound of Formula (I) to (IV) or the isolate can be placed on the target surface before, after or simultaneously with the other agricultural agent.

In one embodiment an organism of the genus *Epicoccum* is *Epicoccum purpurascens* strain SVB-F1 (V10/000331), ICMP2048, ICMP2931, ICMP10458, ICMP10459, ICMP10460, ICMP11503, ICMP15700, ICMP15816 or ICMP16305.

In one embodiment the culture medium comprises a source of nitrate, a source of protein, a source of histidine, or a source of protein comprising histidine, or any combination of any two or more thereof.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

To those skilled in the art to which the invention relates, many changes in construction and differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION OF THE INVENTION

The inventors have surprisingly discovered that *Epicoccum purpurascens* (also known as *Epicoccum nigrum*) produces an antifungal compound having the following formula and that the compound is able to treat or prevent infections by filamentous fungi.

aids storage, transport or handling. Agriculturally acceptable carriers used in compositions for application to plants and plant material are preferably non-phytotoxic or only mildly phytotoxic. A suitable carrier may be a solid, liquid or gas depending on the desired formulation. In one embodiment preferred carriers include polar liquid carriers including but not limited to water, alcohol, mineral oil and vegetable oil. Agriculturally acceptable salts include those that substantially maintain the desired activity of a compound of the invention while also being acceptable for use in agriculture and preferably being non-phytotoxic or only mildly phytotoxic.

The term "alkenyl" means a hydrocarbon radical having at least one double bond including, but not limited to, ethenyl, propenyl, 1-butenyl, 2-butenyl and the like.

The term "alkoxy" means an O-alkyl group wherein "alkyl" is as defined herein, for example, methoxy, ethoxy, and the like.

The term "alkyl" means a straight or branched chain, non-cyclic or cyclic hydrocarbon radical, which may be fully saturated, mono- or polyunsaturated, including di- and multivalent radicals, and may have the number of carbon atoms designated (for example, $C_1$-$C_{10}$ means one to ten carbon atoms). Examples of saturated straight chain alkyls include methyl, ethyl, n-propyl, n-butyl, n-pentyl, n-hexyl and the like. Examples of saturated branched chain alkyls include isopropyl, isobutyl, sec-butyl, test-butyl, isopentyl and the like. Representative saturated cyclic alkyls include cyclopropyl, cyclobutyl, cyclopentyl, cyclohexyl, and the like. An unsaturated alkyl group is one having one or more double or triple bonds. Examples of unsaturated straight chain alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise stated, is also meant to include those derivatives of alkyl defined in more detail below as "alkenyl", "alkynyl", "cycloalkyl" and "alkylene."

The terms "alkylamino" and "dialkyl amino" means one alkyl group or two alkyl groups, respectively, attached through a nitrogen bridge (i.e. —N-alkyl) such as methylamino, ethylamino, dimethylamino, diethylamino, and the like.

The term "alkylcarbonylalkyl," means an alkyl substituted with a —C(=O)alkyl group.

The term "alkylcarbonyloxyalkyl," means an alkyl substituted with a —C(=O)Oalkyl group or a —OC(=O)alkyl group.

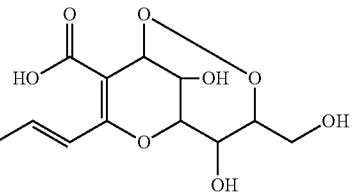

(IV)

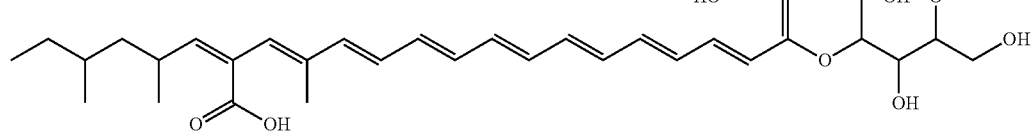

1. Definitions

The term "agriculturally acceptable" is intended to include any material, such as a carrier, that may used in agriculture and that preferably aids application of a compound or composition of the invention to the intended target surface or that The term "alkyloxyalkyl," means an alkyl substituted with an —O-alkyl group.

The term "alkylene" means a divalent radical derived from an alkane, as exemplified by —$CH_2CH_2CH_2CH_2$—. Typically, an alkylene group will have from 1 to 24 carbon atoms.

The term "alkylsulfonyl," means an alkyl group attached through a sulfonyl bridge (i.e. —SO$_2$-alkyl) such as methylsulfonyl, ethylsulfonyl, and the like.

The term "alkylsulfinyl" means an alkyl group attached through a sulfinyl bridge (i.e. S(O)-alkyl) such as methylsulfinyl, ethylsulfinyl, propylsulfinyl, butylsulfinyl, and the like.

The term "alkylthioalkyl" means an alkyl substituted with a —S-alkyl group.

The term "alkynyl" means a hydrocarbon radical having at least one triple bond including, but not limited to, ethynyl, propynyl, 1-butynyl, 2-butynyl and the like.

The term "antifungal" means an ability to antagonise one or more fungi by preventing or controlling a fungal infection as described below. Accordingly an antifungal agent, such as an antifungal compound, isolate or composition, is an agent that is an antagonist of one or more fungi. Such an agent is herein considered to have antifungal activity.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

The term "cycloalkyl" means a cyclic version of "alkyl", and includes di- and poly-homocyclic rings such as decalin and adamantane. Examples of cycloalkyls include cyclopentyl, cyclohexyl, 1-cyclohexenyl, 3-cyclohexenyl, cycloheptyl, and the like.

The terms "halo" or "halogen" means a fluorine, chlorine, bromine, or iodine atom. Additionally, terms such as "fluoroalkyl," are meant to include monofluoroalkyl and polyfluoroalkyl.

The term "haloalkyl" means an alkyl group having at least one hydrogen atom replaced with a halogen, for example trifluoromethyl, and the like.

The term "lower" means a group having 1 to 8 carbon atoms, for example, "lower alkyl", "lower alkenyl", "lower alkynyl", "lower alkylene" and "lower alkoxy" mean an alkyl, alkenyl, alkynyl, alkylene or alkoxy group having 1 to 8 carbon atoms.

The term "hydroxyalkyl" means an alkyl substituted with at least one hydroxyl group.

The term "mono- or di(alkyl)aminoalkyl" means an alkyl substituted with a mono- or di(alkyl)amino.

The term "pharmaceutically acceptable" as used herein refers to carriers, diluents, excipients, compounds, ingredients, materials, compositions, dosage forms and the like, that are within the scope of sound medical judgment, suitable for use in contact with the tissues of the subject in question (e.g. human) without excessive toxicity, irritation, allergic response, or other problem or complication, commensurate with a reasonable benefit/risk ratio. Each carrier, diluent, excipient, and the like, must also be "acceptable" in the sense of being compatible with the other ingredients of the formulation.

The term "plant" means whole plants and includes to plant parts, cuttings as well as plant products including roots, leaves, flowers, seeds, stems, callus tissue, nuts and fruit, bulbs, tubers, corms, grains, cuttings, root stock, or scions, and includes any plant material whether pre-planting, during growth, and at or post harvest. Plants that may benefit from the application of the present invention cover a broad range of agricultural and horticultural crops. The compounds, isolates and compositions of the invention are also suitable for application in organic production systems.

A "strain having the identifying characteristics of [a specified strain]", including a homologue or mutant of the specified strain, is closely related to (i.e., shares a common ancestor with) or derived from the specified strain, but will usually differ from the specified strain in one or more genotypic or phenotypic characteristics. Mutants are generally identifiable through assessment of genetic differences. Homologues are identifiable through assessment of the degree of genetic, biochemical and morphological difference and use of taxonomic methods, including for example analyses such as cladistics. However, a strain having the identifying characteristics of [a specified strain], including a homologue or mutant of the specified strain will retain antifungal efficacy, will be distinguishable from other bacterial strains, and will be identifiable as a homologue or mutant of the parent strain using the techniques described above.

The term "substituted" as used herein with reference to any of the herein defined groups (e.g. alkyl, etc.) means a group or compound wherein at least one hydrogen atom has been replaced by a chemical substituent. In the case of a keto substituent (—(C=O)—) two hydrogen atoms are replaced.

The term "substituent" includes but is not limited to halogen, hydroxyl, cyano, nitro, amino, alkylamino, dialkylamino, alkyl, alkoxy, alkylthio, haloalkyl, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$ and R$_b$ are the same or different and are independently hydrogen, halogen, alkyl, haloalkyl, or substituted alkyl.

The term "subject" is intended to include any animal or target surface that is in need of the treatment or prevention of fungal infection or fungal contamination. Animal subjects include mammals, particularly humans, livestock animals such as cows, sheep, pigs and goats, and companion animals such as horses, dogs and cats.

The term "surroundings" when used in reference to a plant subject includes soil, water, leaf litter, or growth media adjacent to or around the plant or the roots, tubers or the like thereof, adjacent plants, cuttings of said plant, supports, water to be administered to the plant, and coatings including seed coatings. It further includes storage, packaging or processing materials such as protective coatings, boxes and wrappers, and planting, maintenance or harvesting equipment.

The term "target surface" to which a compound or composition of the invention may be applied includes but is not limited to plants and plant surroundings, plant material including but not limited to roots, bulbs, tubers, corms, leaves, flowers, seeds, stems, callus tissue, nuts, grains, fruit, cuttings, root stock, scions, harvested crops including but not limited to roots, bulbs, tubers, corms, leaves, flowers, seeds, stems, callus tissue, nuts, grains, fruit, cuttings, root stock, scions, or any surface that may contact harvested crops including but not limited to harvesting equipment, packaging equipment and packaging material.

The term "treating or preventing a fungal infection" is intended to include preventing or controlling a fungal infection and "controlling" is intended to mean at least maintaining, preferably maintaining or reducing, and more preferably reducing the degree of infection by a fungal pathogen including but not limited to the pathogens listed herein. In one embodiment, "controlling a fungal infection" means the compound, isolate or composition is able to substantially eradicate an existing fungal infection.

The term "thioalkyl" means an alkyl group attached through a sulfur bridge (i.e. —S-alkyl) such as methylthio, ethylthio, and the like.

2. Compounds Obtainable from *Epicoccum purpurascens*

The inventors believe compounds that are structurally related to the compound of Formula (IV) are likely to have similar antifungal activity, including antifungal activity against filamentous fungi, including fungi that are phytopathogens or animal pathogens. Accordingly, the invention relates to a compound of Formula (I) or a salt, solvate, or hydrate thereof

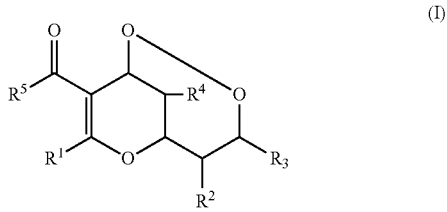

wherein $R^1$ is hydrogen or a $C_1$ to $C_{30}$ alkyl group optionally comprising one or more double bonds, optionally comprising one or more triple bonds, and optionally substituted with one or more groups selected from hydroxyl, halogen, cyano, nitro, amino, alkylamino, dialkylamino, alkyl, alkoxy, alkylthio, haloalkyl, —$NR_aR_b$, —$NR_aC(=O)R_b$, —$NR_aC(=O)NR_aR_b$, —$NR_aC(=O)OR_b$, —$NR_aSO_2R_b$, $OR_a$, —$C(=O)R_a$, —$C(=O)OR_a$, —$C(=O)NR_aR_b$, —$OC(=O)NR_aR_b$, —SH, —$SR_a$, —$SOR_a$, —$S(=O)_2R_a$, —$OS(=O)_2R_a$, —$S(=O)_2OR_a$, wherein $R_a$ and $R_b$ are the same or different and independently selected from the group comprising hydrogen, halogen, hydroxyl, halogen, alkyl, haloalkyl, thioalkyl, and substituted alkyl; and $R^2$, $R^3$, $R^4$ and $R^5$ are independently selected from hydrogen, alkyl, substituted alkyl, alkenyl, substituted alkenyl, alkynyl, substituted alkynyl, alkoxy, substituted alkoxy, alkylthio, substituted alkylthio, haloalkyl, substituted haloalkyl, hydroxyl, halogen, cyano, nitro, amino, alkylamino, dialkylamino, —$NR_aR_b$, —$NR_aC(=O)R_b$, —$NR_aC(=O)NR_aR_b$, —$NR_aC(=O)OR_b$, —$NR_aSO_2R_b$, $OR_a$, —$C(=O)R_a$, —$C(=O)OR_a$, $C(=O)NR_aR_b$, —$OC(=O)NR_aR_b$, —SH, —$SR_a$, —$SOR_a$, —$S(=O)_2R_a$, —$OS(=O)_2R_a$, —$S(=O)_2OR_a$, wherein $R_a$ and $R_b$ are the same or different and independently selected from the group comprising hydrogen, halogen, alkyl, haloalkyl, thioalkyl, and substituted alkyl.

In various embodiments the invention also relates to compounds of Formula (II), (III) and (IIIA) described above.

In one embodiment the compound of Formula (I) is the compound of Formula (IV)

It should be understood that a certain compound may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; (+) and (−) forms; keto-, enol-, and enolate-forms; α- and β-forms; axial and equatorial forms; boat-, chair-, twist-, envelope-, and halfchair-forms; and combinations thereof, hereinafter collectively referred to as "isomers" (or "isomeric forms").

Some compounds of Formula (I) to (IV) have at least one asymmetrical carbon atom and therefore all isomers, including enantiomers, stereoisomers, rotamers, tautomers and racemates of the compounds are contemplated as being part of this invention. The invention includes D and L isomers in both pure form and in admixture, including racemic mixtures. Isomers can be prepared using conventional techniques, either by reacting optically pure or optically enriched starting materials or by separating isomers of a compound of the invention. Isomers may also include geometric isomers, e.g., when a double bond is present.

Note that, except as discussed below for tautomeric forms, specifically excluded from the term "isomers," as used herein, are structural (or constitutional) isomers (i.e., isomers that differ in the connections between atoms rather than merely by the position of atoms in space). For example, a reference to a methoxy group, —$OCH_3$, is not to be construed as a reference to its structural isomer, a hydroxymethyl group, —$CH_2OH$. However, a preference to a class of structures may well include structurally isomeric forms falling within that class (e.g., $C_{1-7}$ alkyl includes n-propyl and iso-propyl; butyl includes iso-, sec-, and tert-butyl).

The above exclusion does not relate to tautomeric forms, for example, keto-, enol-, and enolate-forms, as in, for example, the following tautomeric pairs: keto/enol, imine/enamine, amide/imino alcohol, amidine/amidine nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

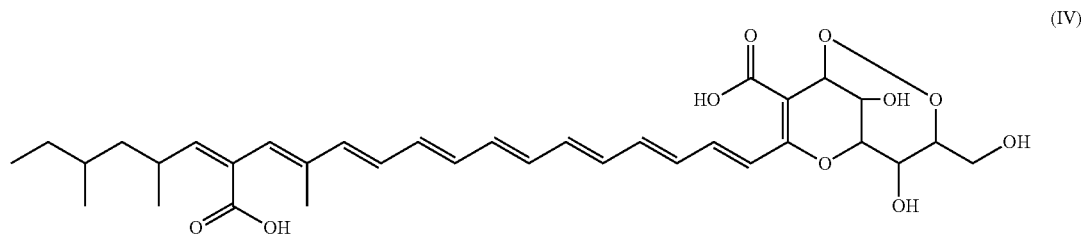 [SMILES: CCC(C)CC(C)/C=C(/C=C(C)/C=C/C=C/C=C/C=C/C=C/C=C/C1=C(C(=O)O)C2OOC(CO)C(O)C(O1)C2O)C(=O)O]

Also unless otherwise specified, a reference to a particular compound also includes ionic, salt, solvate, hydrate, and protected forms of the compound.

If the compound is cationic, or has a functional group which may be cationic (e.g., —NH— may be —NH$_3$+), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, anions from the following organic acids: acetic, propionic, succinic, gycolic, stearic, lactic, malic, tartaric, citric, ascorbic, maleic, hydroxymaleic, phenylacetic, glutamic, benzoic, salicylic, sulfanilic, 2-acetyoxybenzoic, fumaric, toluenesulfonic, methanesulfonic, ethane disulfonic, oxalic, isethionic, and valeric.

It may be convenient or desirable to prepare, purify, or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, or handle the active compound in a chemically protected form. The term "chemically protected form," as used herein, relates to a compound in which one or more reactive functional groups are protected from undesirable chemical reactions, that is, are in the form of a protected or protecting group (also known as masked or masking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic J Synthesis (T. Green and P. Wuts, Wiley, 1991), incorporated herein by reference.

3. Isolation of Compounds of Formula (IV) from *Epicoccum purpurascens*

The compound of Formula (IV) can be isolated from *Epicoccum purpurascens* (also known as *Epicoccum nigrum*) by culturing the organism and then extracting the compounds to the desired degree of purity.

Accordingly, in one embodiment the compound of Formula (I) to (IV) is obtained or obtainable from an organism of the genus *Epicoccum*. In another embodiment the compound of Formula (I) to (IV) is obtained or obtainable from *Epicoccum purpurascens*. In a further embodiment the compound of Formula (I) to (IV) is obtained or obtainable from *Epicoccum purpurascens* strains SVB-F1 (V10/000331), ICMP2048, ICMP2931, ICMP10458, ICMP10459, ICMP10460, ICMP11503, ICMP15700, ICMP15816 or ICMP16305. As shown in the examples below, each of these strains produces the compound of Formula (IV). The *Epicoccum purpurascens* strain SVB-F1 is on deposit under accession number V10/000331 at the National Measurement Institute, Australia, deposited on 18 Mar. 2010. The ICMP strains are available from the International Collection of Microorganisms from Plants (ICMP) administered by Landcare Research, New Zealand (see http://nzfungi.landcareresearch.co.nz/icmp/search_cultures.asp—last accessed 23 Nov. 2009). *Epicoccum purpurascens* strains are also available from the American Type Culture Collection (ATCC), including but not limited to the strains ATCC 10999, ATCC 32948, ATCC 34417, ATCC 34547, ATCC 34929, ATCC 44336, ATCC 46473, ATCC 46878, ATCC 46880, ATCC 46881, ATCC 58875, ATCC 62191, and ATCC 66091. These strains discussed above may also be used in the methods of culturing organisms of the genus *Epicoccum* described herein.

The compound of Formula (IV) can be isolated from *Epicoccum purpurascens* by culturing the organism under submerged conditions in industrial bioreactors known in the art and then extracting the compounds to the desired degree of purity using centrifugation or membrane filtration or both to remove suspended solids, biomass, fungal spores and soluble proteins (such as enzymes). Alternatively, the compound of Formula (IV) can be isolated from *Epicoccum purpurascens* by culturing the organism on a solid substrate using solid fermentation techniques known in the art and then extracted with a suitable environmentally-friendly and non-toxic solvent (including but not limited to methanol, ethanol, ethyl acetate, for example) and further extracted to the desired degree of purity using centrifugation or membrane filtration or both to remove suspended solids, biomass, fungal spores and soluble proteins (such as enzymes). In both alternatives the product of centrifugation or the filtrate can be further purified if necessary by column chromatography using acid silica or any other appropriate polar solid matrix. Other suitable known alternatives for isolating the compounds will be apparent to those skilled in the art.

The inventors have found that compounds of Formula (IV) may usefully be produced by culturing an organism of the genus *Epicoccum* in a culture medium comprising nitrate, protein or histidine (data not shown). Accordingly, in one embodiment the culture medium comprises a source of nitrate, a source of protein, a source of histidine, or a source of protein comprising histidine, or any combination of any two or more thereof. Examples of useful sources of nitrate include but are not limited to nitrate salts, any agriculturally or pharmaceutically acceptable source of nitrate, sodium nitrate, magnesium nitrate, potassium nitrate and calcium nitrate, or any combination of any two or more thereof, and other useful nitrate sources will be apparent to those skilled in the art. Examples of useful sources of protein include but are not limited to peptone, yeast extract, and potato extract, or any combination of any two or more thereof, and other useful protein sources will be apparent to those skilled in the art. Examples of useful sources of histidine include but are not limited to histidine as a free amino acid, and dipeptides, tripeptides, oligopeptides or polypeptides comprising histidine, or any combination of any two or more thereof, and other useful histidine sources will be apparent to those skilled in the art.

4. Target Agricultural Pathogens

The compounds, isolates, are compositions of the invention are useful to treat or prevent infections caused by filamentous fungi. In one embodiment the fungus comprises a filamentous fungus and the fungal infection comprises a filamentous fungal infection.

In one embodiment the fungus is of the family Gnomoniaceae (for example, *Apiognomonia supraseptata*), Cortiaceae (for example, *Rhizoctonia solani*), Magnoporthaceae (for example, *Magnaporthe grisea*), Mycosphaerellaceae, Pleosporaceae (for example, *Alternaria alternata*), Sclerotiniaceae (for example, *Botrytis cinerea* or *Sclerotinia sclerotiorum*), Typhulaceae (for example *Sclerotium cepivorumi*), Valsaceae (for example, *Phomopsis viticola*), or Venturiaceae (for example, *Venturia inaequalis*).

In another embodiment the fungus is of the genus *Apiognomonia* (for example, *Apiognomonia supraseptata*), *Alternaria* (for example, *Alternaria alternata*), *Botrytis* (for example, *Botrytis cinerea*), *Botryotinia, Magnaporthe* (for example, *Magnaporthe grisea*), *Phomopsis* (for example, *Phomopsis viticola*), *Rhizoctonia* (for example, *Rhizoctonia solani*), *Sclerotinia* (for example, *Sclerotinia sclerotiorum*), *Sclerotium* (for example, *Sclerotium cepivorumi*), or Venturiaceae (for example, *Venturia inaequalis*).

In yet another embodiment the fungus is *Apiognomonia supraseptata*, *Alternaria alternata*, *Botrytis cinerea*, *Botryotinia* spp., *Magnaporthe grisea*, *Phomopsis viticola*, *Rhizoctonia solani*, *Sclerotinia sclerotiorum*, *Sclerotium cepivorumi*, or *Venturia inaequalis*.

Species from the above families and genus are responsible for many agricultural plant diseases. For example, *Botrytis cinera* is responsible for blossom blights and fruit rots, and *Rhizoctonia Solani* is responsible for 'wire stem'. Other species from the listed families and genus are responsible for diseases such as 'pitting disease', 'ryegrass blast' and 'southern blight'.

Other fungal infections that may be treated or prevented using the compounds, isolates, compositions and methods of the invention include but are not limited to anthracnose (for example, oak anthracnose), canker (for example, stem canker of tomato), ringspot disease (for example, ringspot disease of pear), blight and lesions of vegetables (for example, parsley leaf blight), fruit rot (for example, grey rot and noble rot of grapes), blast disease or bright disease (for example, rice rotten neck, rice seedling blight, blast of rice, oval leaf spot of graminea, pitting disease, ryegrass blast, and johnson spot), cane and leaf spot (for example, leaf and berry spot of grapes), damping off (for example, death of seedlings in agriculture), wire stem (for example, disease of cabbage, cauliflower and related plants), white mould (for example, white mould in soy beans and dry edible beans), wilt or stalk rot (for example, steam rot in canola), southern blight (blight of wheat and tomato), and scab lesions (for example, apple scab).

It should be understood that filamentous fungi are readily identifiable as such by those skilled in the art and that the compounds, isolates, compositions and methods of the invention are equally useful in treating or preventing fungal infections caused by those other filamentous fungi. Equally, the compounds, isolates and compositions of the invention may be assayed for activity against any fungal species according to the methods described in the examples below.

5. Target Animal Pathogens

In other embodiments the fungus comprises a filamentous fungus that is an animal pathogen and the fungal infection comprises a filamentous fungal infection of animals.

In one embodiment the fungus is of the family Dothioraceae (for example, *Hortaea werneckii*, syn. *Phaeoannellomyces werneckii*), Trichosporonaceae (for example, *Trichosporon beigelii*), Piedraiaceae (for example, *Piedraia hortae*), Arthrodermataceae (for example, *Trichophyton rubrum*, *Microsporum gypseum* or *Epidermophyton floccosum*), Sphaeropsidaceae (for example, *Scytalidium dimidiatum*, syn *Hendersonula toruloidea* or *Scytalidium hyalinum*), or Microascaceae (for example, *Scopulariopsis brevicaulis*).

In one embodiment the fungus is of the genus *Hortaea* (for example, *Hortaea werneckii*, syn. *Phaeoannellomyces werneckii*), *Trichosporon* (for example, *Trichosporon beigelii*, *Piedraia* (for example, *Piedraia hortae*), *Trichophyton* (for example, *Trichophyton rubrum*), *Microsporum* (for example, *Microsporum gypseum*), *Epidermophyton* (for example, *Epidermophyton floccosum*), *Hendersonula* (for example, *Hendersonula toruloidea*), *Scytalidium* (for example, *Scytalidium hyalium*), or *Scopulariopsis* (for example, *Scopulariopsis brevicaulis*).

It should be understood that the compounds, isolates and compositions of the invention may be assayed for activity against any fungal species that is pathogenic to animals, particularly humans, according to the methods described in the examples below.

6. Agricultural Compositions of the Invention

Compositions useful herein included any agriculturally or pharmaceutically acceptable composition that can carry a compound of Formula (I) to (IV) or a salt, solvate or hydrate thereof, or an isolate of the invention, as well as compositions suitable for maintaining the viability of *Epicoccum purpurascens* SVB-F1 or a strain having the identifying characteristics of *Epicoccum purpurascens* SVB-F1. The compositions of the invention, in various embodiments, are sprayable and may be sprayed onto a subject in need thereof, or formulated as a concentrate that is sprayable on addition of agriculturally acceptable carriers and/or spray adjuvants. The compositions of the present invention may also be a solid, such as a powder, that is placed on to the target surface. Preferred compositions of the invention are shelf stable. The term "shelf stable" is intended to mean that a composition of the invention does not separate out into separate phases, develop offensive odours and/or develop microbial growth.

Compositions of the invention may be formulated as, for example, concentrates, solutions, sprays, aerosols, immersion baths, dips, emulsions, wettable powders, soluble powders, suspension concentrates, dusts, granules, water dispersible granules, microcapsules, pastes, gels and other formulation types by well-established procedures. These procedures include mixing and/or milling of the active ingredients with agriculturally acceptable carrier substances, such as fillers, solvents, excipients, surfactants, suspending agents, spreaders/stickers (adhesives), antifoaming agents, dispersants, wetting agents, drift reducing agents, auxiliaries and adjuvants. Depending on the format chosen, compositions may be formulated for methods of application such as injection, rubbing or brushing, as are known in the art. Indirect applications of the composition to the plant surroundings or environment such as soil, water, or as seed coatings are potentially possible.

The compositions of the present invention may further comprise components such as liquid or solid carriers, binders, fillers and other agriculturally or pharmaceutically suitable additives.

In one embodiment the agriculturally acceptable carriers maybe selected from the group comprising fillers, solvents, excipients, surfactants, suspending agents, spreaders/stickers (adhesives), antifoaming agents, dispersants, wetting agents, drift reducing agents, auxiliaries, adjuvants or a mixture thereof.

In one embodiment solid carriers include but are not limited to mineral earths such as silicic acids, silica gels, silicates, talc, kaolin, attapulgus clay, limestone, lime, chalk, bole, loess, clay, dolomite, diatomaceous earth, aluminas calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders and the like. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black;

water soluble polymers, resins, waxes; or solid fertilizers. Such solid compositions may, if desired, contain one or more compatible wetting, dispersing, emulsifying or coloring agents which, when solid, may also serve as a diluent.

In one embodiment the carrier may also be liquid, for example, water; sugar solutions; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulfoxide, or N-methylpyrrolidone; liquefied gases; or the like or a mixture thereof.

In one embodiment surfactants include nonionic surfactants, anionic surfactants, cationic surfactants and/or amphoteric surfactants and promote the ability of aggregates to remain in solution during spraying.

Spreaders and stickers promote the ability of the compositions of the invention to adhere to plant surfaces. Examples of surfactants, spreaders and stickers include but are not limited to Tween and Triton (Rhom and Hass Company), Fortune®, Pulse, C. Daxoil, Codacide Oil®, D-C talc, Supamet Oil, Bond®, Penetrant, Glowelt® and Freeway, alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Wetting agents reduce surface tension of water in the composition and thus increase the surface area over which a given amount of the composition may be applied. Examples of wetting agents include but are not limited to salts of polyacrylic acids, salts of lignosulfonic acids, salts of phenolsulfonic or naphthalenesulfonic acids, polycondensates of ethylene oxide with fatty alcohols or fatty acids or fatty esters or fatty amines, substituted phenols (particularly alkylphenols or arylphenols), salts of sulfosuccinic acid esters, taurine derivatives (particularly alkyltaurates), phosphoric esters of alcohols or of polycondensates of ethylene oxide with phenols, esters of fatty acids with polyols, or sulfate, sulfonate or phosphate functional derivatives of the above compounds.

In one embodiment the preferred method of applying the compound or composition of the invention is to spray a dilute or concentrated solution by handgun or commercial airblast.

A carrier which provides for slow or delayed release of a compound of the invention may also be included in a composition of the invention.

The compositions of the present invention may be used alone or in combination with one or more other agricultural agents, including pesticides, insecticides, acaracides, additional fungicides, bactericides, herbicides, antibiotics, antimicrobials, nemacides, rodenticides, entomopathogens, pheromones, attractants, plant growth regulators, plant hormones, insect growth regulators, chemosterilants, microbial pest control agents, repellents, viruses, phagostimulents, plant nutrients, plant fertilisers and biological controls. When used in combination with other agricultural agents the administration of the two agents may be separate, simultaneous or sequential. Specific examples of these agricultural agents are known to those skilled in the art, and many are readily commercially available.

Examples of plant nutrients include but are not limited to nitrogen, magnesium, calcium, boron, potassium, copper, iron, phosphorus, manganese, molybdenum, cobalt, boron, copper, silicon, selenium, nickel, aluminum, chromium and zinc.

Examples of antibiotics include but are not limited to oxytetracyline and streptomycin.

Examples of fungicides include but are not limited to the following classes of fungicides: carboxamides, benzimidazoles, triazoles, hydroxypyridines, dicarboxamides, phenylamides, thiadiazoles, carbamates, cyano-oximes, cinnamic acid derivatives, morpholines, imidazoles, beta-methoxy acrylates and pyridines/pyrimidines.

Further examples of fungicides include but are not limited to natural fungicides, organic fungicides, sulphur-based fungicides, copper/calcium fungicides and elicitors of plant host defences.

Examples of natural fungicides include but are not limited to whole milk, whey, fatty acids or esterified fatty acids.

Examples of organic fungicides include but are not limited to any fungicide which passes an organic certification standard such as biocontrol agents, natural products, elicitors (some of may also be classed as natural products), and sulphur and copper fungicides (limited to restricted use). An example of a sulphur-based fungicide is Kumulus™ DF (BASF, Germany). An example of a copper fungicide is Kocide® 2000 DF (Griffin Corporation, USA). Examples of elicitors include but are not limited to chitosan, Bion™, BABA (DL-3-amino-n-butanoic acid, β-aminobutyric acid) and Milsana™ (Western Farm Service, Inc., USA).

In some embodiments non-organic fungicides may be employed. Examples of non-organic fungicides include but are not limited to Bravo™ (for control of PM on cucurbits); Supershield™ (Yates, NZ) (for control of *Botrytis* and PM on roses); Topas® 200EW (for control of PM on grapes and cucurbits); Flint™ (for control of PM on apples and cucurbits); Amistar® WG (for control of rust and PM on cereals); and Captan™, Dithane™, Euparen™, Rovral™, Scala™, Shirlan™, Switch™ and Teldor™ (for control of *Botrytis* on grapes).

Examples of pesticides include but are not limited to azoxystrobin, bitertanol, carboxin, $Cu_2O$, cymoxanil, cyproconazole, cyprodinil, dichlofluamid, difenoconazole, diniconazole, epoxiconazole, fenpiclonil, fludioxonil, fluquiconazole, flusilazole, flutriafol, furalaxyl, guazatin, hexaconazole, hymexazol, imazalil, imibenconazole, ipconazole, kresoxim-methyl, mancozeb, metalaxyl, R-metalaxyl, metconazole, oxadixyl, pefurazoate, penconazole, pencycuron, prochloraz, propiconazole, pyroquilone, SSF-109, spiroxamin, tebuconazole, thiabendazole, tolifluamid, triazoxide, triadimefon, triadimenol, triflumizole, triticonazole and uniconazole.

An example of a biological control is the BotryZen™ biological control agent comprising *Ulocladium oudemansii*.

Confirmation of the ability of compositions of the invention to treat fungal growth may be obtained by inoculating plant material with a target organism and then applying a compound, isolate or composition of the invention. Efficacy is confirmed by a reduction in the degree of growth or the disappearance of the target organism compared to an untreated control.

7. Therapeutic Compositions of the Invention

A composition useful herein may be formulated as a food, drink, food additive, drink additive, dietary supplement, nutritional product, medical food, enteral or parenteral feeding product, meal replacement, cosmeceutical, nutraceutical, or pharmaceutical, or as a coating or other component of a medical device. Appropriate formulations may be prepared by an art skilled worker with regard to that skill and the teaching of this specification. Compositions useful herein include any composition that is able to carry a compound of Formula (I) to (IV) or an isolate of the invention.

In one embodiment the composition is in the form of a powder, a tablet, a caplet, a pill, a hard or soft capsule or a lozenge. In another embodiment the composition is in the form of a cachet, a dispensable powder, granules, a suspension, an elixir, a liquid, a drink, or any other form that can be added to food or drink, including for example water or fruit juice. In a further embodiment the composition is an enteral product, a solid enteral product or a liquid enteral product. In yet another embodiment, the composition is in the form of a cream, ointment, paste, drop solution including eye drops or ear drops, inhaler, inhalable composition, dressing, pad, or spray.

The compositions useful herein may be formulated to allow for administration to a subject by any chosen route, including but not limited to oral or nasal (including by inhalation), vaginal, rectal or parenteral (including topical, subcutaneous, intramuscular and intravenous) administration. Those skilled in the art will appreciate that the route of administration to a subject will typically take into account the purpose for which the composition is being administered for example, where a pharmaceutical composition of the invention is being administered to treat a disease or disorder, the route of administration will typically be chosen taking into account the nature of the disease or disorder. Accordingly, exemplary compositions for the treatment of skin infections or infections of mucosal membranes may be formulated for topical administration.

In general, for oral administration a dietary (a food, food additive or food supplement for example), nutraceutical or pharmaceutical composition useful herein may be formulated by a skilled worker according to known formulation techniques. Thus, a pharmaceutical composition useful according to the invention may be formulated with an appropriate pharmaceutically acceptable carrier (including excipients, diluents, auxiliaries, and combinations thereof) selected with regard to the intended route of administration and standard pharmaceutical practice. See for example, Remington's Pharmaceutical Sciences, 16th edition, Osol, A. Ed., Mack Publishing Co., 1980.

Administration of a compound or composition of the invention by a first administration route accompanied by separate, simultaneous or sequential administration of one or more additional agents, including one or more other antifungal agents, by the same or a second administration route is contemplated; for example, oral or topical administration of a compound or composition of the invention accompanied by oral or topical administration of the at least one additional agent.

Also, the compositions useful herein may contain one or more additional agents as required, including one or more additional antifungal agents, or emulsifying, antioxidant, flavouring or colouring agents, or have an enteric coating. Suitable enteric coatings are known. Enteric coatings surrounding the active ingredients and prevent the release of the active ingredients in the stomach but allow release after the dosage form has left the stomach. Compositions useful herein may be adapted for immediate, delayed, modified, sustained, pulsed or controlled release of a compound of the invention.

Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent. Parenteral dosage forms include aqueous solutions, isotonic saline or glucose solutions comprising the active agent, or other well-known pharmaceutically acceptable carriers. Solubilising agents well-known to those familiar with the art can be used as pharmaceutical excipients. Injectable dosage forms may be formulated as liquid solutions or suspensions. Solid forms suitable for solution in, or suspension in, liquid prior to injection may also be prepared.

Sustained-release preparations may be prepared. Suitable examples of sustained-release preparations include semi-permeable matrices of solid hydrophobic polymers containing the desired antifungal agents. The matrices may be in the form of shaped articles, e.g., films, or microcapsules. Examples of sustained-release matrices include polyesters, hydrogels (for example, poly(2-hydroxyethyl-methacrylate), or poly(vinylalcohol)), polylactides (see U.S. Pat. No. 3,773,919), copolymers of L-glutamic acid and ethyl-L-glutamate, non-degradable ethylene-vinyl acetate, and degradable lactic acid-glycolic acid copolymers such as the LUPRON DEPOT™ (injectable microspheres composed of lactic acid-glycolic acid copolymer and leuprolide acetate).

Topical formulations may be prepared as lotions, creams, ointments, pastes or salves using known carriers for such applications. Such formulations may be administered directly, for example, applied directly on to a site of infection, a wound, sprayed onto a surgical site, etc, or may be applied indirectly, such as by impregnation into a bandage or dressing or sprayed onto surgical equipment, dressings and the like.

In various embodiments, the at least one additional agent is an antifungal agent, such as a polyene antifungal, such as natamycin, rimocidin, filipin, nystatin, amphotericin B, candicin; imidazoles, such as miconazole, ketoconazole, clotrimazole, econazole, bifonazole, butoconazole, fenticonazole, isoconazole, oxiconazole, sertaconazole, sulconazole, or tioconazole; triazoles, such as fluconazole, itraconazole, isavuconazole, ravuconazole, posaconazole, voriconazole, or terconazole; thiazoles such as abafungin; allylamines, such as terbinafine, amorolfine, naftifine, or butenafine; echinocandins, such as anidulafungin, caspofungin, or micafungin; others antifungal agents such as benzoic acid, ciclopirox, tolnaftate, undecylenic acid, flucytosine or 5-fluorocytosine, griseofulvin, haloprogin, sodium bicarbonate, allicin, one or more essential oils, tea tree oil, citronella oil, iodine, lemon grass, olive leaf, orange oil, palmarosa oil, patchouli, lemon myrtle, neem seed oil, coconut oil, zinc, or selenium.

The efficacy of a composition useful herein can be evaluated both in vitro and in vivo. See, e.g., the examples below. Briefly, in one embodiment the composition can be tested for its ability, to for example, inhibit fungal growth in vitro. For in vivo studies, the composition can be administered to an animal (e.g., a mouse) and its effects on fungal infection, or one or more symptoms of the fungal disease or disorder are then assessed. Based on the results, an appropriate dosage range, frequency, and administration route can be determined.

It should be understood that the additional agents listed above may also be employed in a method of the invention where they are administered separately, simultaneously or sequentially with a compound, isolate or composition useful herein.

As will be appreciated, the dose of the composition administered, the period of administration, and the general administration regime may differ between subjects depending on such variables as the severity of symptoms of a subject, the type of disorder to be treated, the mode of administration chosen, and the age, sex and/or general health of a subject. However, by way of general example, from about 1 mg to about 5000 mg per kg body weight, about 1 mg to about 4000 mg per kg body weight, about 1 mg to about 3000 mg per kg body weight, about 1 mg to about 2000 mg per kg body weight, about 1 mg to about 1000 mg per kg body weight, or about 1 mg to about 500 mg per kg body weight of a compound useful herein is administered, per administration or per day, preferably about 50 to about 1000 mg per kg, preferably per day. Administration may include a single dose, such as a single daily dose, or administration of a number of discrete divided doses as may be appropriate. A person of ordinary skill in the art will be able to determine without undue experimentation, having regard to that skill and this disclosure, an effective dosage regime (including dose and timing of administration) for a given condition.

When used in combination with an additional agent, the administration of a compound useful herein and the other agent may be separate, simultaneous or sequential. Simultaneous administration includes the administration of a single dosage form that comprises all components or the administration of separate dosage forms at substantially the same time. Separate or sequential administration includes administration according to different schedules, preferably so that there is an overlap in the periods during which the composition useful herein and other therapeutic agent are provided.

Additionally, it is contemplated that a composition in accordance with the invention may be formulated with additional active ingredients which may be of benefit to a subject in particular instances. For example, therapeutic agents that target the same or different facets of the disease process may be used.

The compounds or compositions of the invention may be incorporated into or onto medical devices and medical supplies. The medical devices or supplies may be coated or impregnated with compositions of the invention by known methods.

Various aspects of the invention will now be illustrated in non-limiting ways by reference to the following examples.

EXAMPLES

1. Materials and Methods (a) Fungal Strains

An *Epicoccum purpurascens* strain SVB-F1 was isolated in a laboratory environment as a contaminant of other cultures. It was identified based on its morphological characteristics, on its strong anti-fungi activity against different filamentous fungi, and on the sequence of its 18S rDNA (ITS region) (data not shown). The compound of Formula (IV) was identified and isolated from the exudate of this strain. Other *Epicoccum purpurascens* strains obtained subsequently and tested were ICMP1732, ICMP2048, ICMP2931, ICMP10458, ICMP10459, ICMP10460, ICMP11503, ICMP13352, ICMP15700, ICMP15816 and ICMP16305, all available from Landcare Research, New Zealand. Active spore suspension and mycelia on agar slants were kept preserved in glycerol saline at −80° C.

The phytopathogenic fungi *Apiognomonia supraseptata* SVB-F2 was isolated from plant material and identified based on the sequence of its 18S rDNA (ITS region).

The phytopathogenic fungi *Botrytis cinera* ICMP16621, *Sclerotinia sclerotiorum* ICMP13844, *Alternaria alternate* ICMP1099-96, *Phomopsis viticola* ICMP5537, *Mycosphaerella graminicola* ICMP12504-95, *Rhizoctonia solani* ICMP11620, *Magnaporthe grisea* ICMP14481, *Sclerotium cepivorum* ICMP10916-91, and *Venturia inaequalis* ICMP4095-96 were all obtained from Landcare Research, New Zealand.

(b) *Epicoccum purpurascens* strain SVB-F1 (V10/000331)

*Epicoccum purpurascens* strain SVB-F1 is on deposit under accession number V10/000331 at the National Measurement Institute, Australia, deposited 18 Mar. 2010 in accordance with the Budapest Treaty. *E. purpurascens* (syn. *E. nigrum*, Eukaryota; Fungi; Dikarya; Ascomycota; Saccharomyceta; Pezizomycotina; Leotiomyceta; Dothideomyceta; Dothideomycetes; *Epicoccum*) is a saprophytic filamentous fungus usually isolated from senescing plant tissues and soil. It grows slowly to form white mycelial biomass. This strain deposit will be maintained without restriction in the National Measurement Institute depository for a period of 30 years, or 5 years after the last request, or for the effective life of the patent, whichever is longer, and will be replaced if the deposit becomes non-viable during that period. Upon grant of a patent, all restrictions imposed by the depositor on the availability to the public of the deposited biological material will be irrevocably removed.

Morphology

Strain SVB-F1 grows rapidly and produces woolly to cottony or felty colonies on potato dextrose agar at 25° C. From the front, the colonies are yellow to orange, orange to red or pink initially and become greenish brown to black by aging. From the reverse, the same colour is observed but is usually more intense than in the front view. *Epicoccum* may produce a diffusible pigment which turns the colour of the inoculated medium to yellow, orange, red or brown. Black dots (100-2000 μm in diameter) may be observed macroscopically on the colony surface. These are the tufts of hyphae which have conidiophores on their surface. These tufts of hyphae are cushion-shaped and nonconvoluted and are called sporodochia.

Metabolism

Strain SVB-F1 grows on a wide range of substrates and is able to grow on minimal mineral medium with any carbohydrate as carbon source and ammonia or nitrate as nitrogen source. Optimal growth temperature is 25° C. and the organism can tolerate a wide range of pH (3-10).

(c) Other Organisms

*Candida albicans* SC5614, *Candida utilis* 02/DO0981, *Saccharomyces cerevisiae* BM45, *Staphylococcus epidermis* SVB-B12, *Escherichia coli* SVB-B11 and *Pseudomonas aeruginosa* SVB-B10 were obtained from culture collections held at the University of Auckland, Auckland, New Zealand.

(d) Growth Media

The following agar-based culture media were used. Czapek solution yeast extract agar (CYA) containing per liter: Sucrose (30 g), sodium nitrate (2 g), dipotassium phosphate (1 g), magnesium sulphate (0.5 g), potassium chloride (0.5 g), ferrous sulphate (0.01 g), yeast extract (6 g) and agar (15 g); pH 7.3. Yeast extract peptone dextrose agar (YPD) containing per liter: yeast extract (6 g), peptone (6 g), D-glucose (10 g) and agar (15 g); pH 5.5. Potato dextrose agar (PDA) containing per liter: infusion suspension resulted from diced unpeeled potatoes (400 g) boiled for 40 min in distilled water, D-glucose (10 g), agar (15 g); pH 5.5. Minimal mineral agar medium (MM) containing per liter: D-glucose (10 g), ammonium sulphate (6 g), monopotassium hydrogen phosphate (3 g), magnesium sulphate heptahydrate (0.5 g), vitamins and trace elements according to Verduyn et al.; pH 5.5/7.0.

(e) Growth Conditions

Production of antifungal pigment by *E. purpurascens* strain SVB-F1 was tested on three different complex culture media (CYA, YPD and PDA) as well as on minimal mineral medium (MM) at pH 7 supplemented or not with individual amino acids (5 g/L). All cultures were carried out using Petri dishes incubated at 25° C. for 10 days.

(f) Extraction and Purification of the Biologically Active Compound

Ten day old *E. purpurascens* SVB-F1 cultures on agar plates were diced and transferred to 250 mL Schott bottle containing 50 mL of methanol. The flasks were shaken for 30 min at room temperature in the dark. The methanol extracts were separated from the fungal biomass and agar by filtration using cotton-wool followed by filtration using nitrocellulose membrane (0.22 μm).

Pigmented compounds were pre-purified from the methanol extract by solid-phase extraction using SPE DSC-Si silica 5 g cartridges (Discovery®, Supelco, Bellefonte, USA). The cartridges were primed with 3-volumes (20 mL) of deionised water, followed by 3-volumes (20 mL) methanol, 3-volumes (20 mL) of acetonitrile and 1-volume (20 mL) of acetonitrile/methanol mixture (1:1). Sample dissolved in acetonitrile/methanol mixture (1:1) was eluted with the same solvent mixture and the pigmented fraction was collected and dried under air-flow in the dark.

The air-dried pigmented residues were washed with hexane to remove non-polar compounds. Residual hexane was then removed by evaporation and the precipitate resuspended in deionised water at pH 10. Pigmented compounds were then further purified from the pre-purified extracts by HPLC (Beckmann, USA) using UV detection at 360 nm. Pigments were separated on a Gemini-NX C18 column (Phenomenex) at room temperature. Two solvents, (A) deionised water at pH 10 (NH4OH), and (B) methanol/isopropanol (4:1), were used in combination as the mobile phase at a flow of 1 mL/min. A gradient from 0-12 min comprised 25% to 100% (B), holding for 1 min and returning back to 25% over the next 7 min. Pigmented fractions eluting from the column were collected and their retention time recorded.

(g) Stability Tests

Stability was determined by re-suspending between 0.3 to 0.5 mg/mL of purified pigmented compound of Formula (IV) in different testing solutions according to Table 1, and measuring the absorbance at 428 nm every 24 hours for fifteen days. The test samples were kept in glass vials under constant incandescent light (except for the temperature stability test).

TABLE 1

Stability of the compound of Formula (IV)

| Condition | Specific condition | Initial absorbance (428 nm) | Final absorbance (428 nm)# |
|---|---|---|---|
| pH stability | 3 | 1.46 | 1.45 |
| | 5 | 1.67 | 1.67 |
| | 7 | 2.05 | 2.05 |
| | 8 | 2.09 | 2.08 |
| | 10 | 2.09 | 2.09 |
| Stability to some common acids | Citric acid | 1.53 | 0.51 |
| | Acetic acid | 1.61 | 0.66 |
| | Malic acid | 1.53 | 0.38 |
| | Lactic acid | 1.52 | 0.68 |
| Stability to some common alkalis* | NaHCO$_3$ | 2.08 | 2.08 |
| | Na$_2$CO$_3$ | 2.13 | 2.12 |
| | NaOH | 2.05 | 2.04 |
| Stability to presence of sugars* | Dextrose | 2.08 | 2.08 |
| | Sucrose | 2.08 | 2.07 |
| | Fructose | 2.02 | 2.03 |
| Stability to light | In water | 2.05 | 1.82 |
| | In methanol | 2.04 | 2.04 |
| | In ethanol 5% v/v | 2.04 | 2.04 |
| Stability to temperature | −20° C. in water | 2.08 | 2.07 |
| | −20° C. in methanol | 2.05 | 2.06 |
| | 4° C. in water | 2.08 | 2.06 |
| | 4° C. in methanol | 2.05 | 2.03 |
| | 60° C. in water | 2.08 | 2.06 |
| | 60° C. in methanol | 2.05 | 2.04 |
| | 100° C. in water | 2.08 | 2.07 |
| Stability to microwave radiation | 5 min, domestic microwave (1000 W) | 2.05 | 2.04 |

*10% w/w;
after 10 days (except for temperature and microwave radiation tests)

(h) Biological Activity Tests—Antagonism by *E. purpurascens* SVB-F1

The antagonistic properties of *E. purpurascens* SVB-F1 against other filamentous fungi were assessed by co-culture on YPD plates incubated at 25° C. for 7 days in the dark. The fungi tested were *Apiognomonia supraseptata* SVB-F2, *Botrytis cinera* ICMP16621 (Landcare Research, New Zealand) and *Sclerotinia sclerotiorum* ICMP13844 (Landcare Research, New Zealand).

(i) Biological Activity Test—Inhibition of Mycelial Growth

The activity of the compound of Formula (IV) purified by HPLC was tested using agar diffusion assays against mycelial growth of *A. supraseptata* SVB-F2, *B. cinera* ICMP16621, and *S. sclerotiorum* ICMP13844. The fungal strains were grown on YPD agar. Test compounds were absorbed onto individual paper disks (6 mm diameter) or directly into the agar through a 1-mm hole at 20 μL/disk of pigment solution in phosphate buffer (pH 7.4). Phosphate buffer was used as a negative control. The assay plates were incubated at 25° C. for 5 days and examined for the presence of a zone of inhibition.

(j) Biological Activity Test—Inhibition of Spore Germination

The activity of the compound of Formula (IV) against the spore germination of different phytopathogens was carried out in 12-well microtitre plates containing 200 μL of fungal spore suspension (~106 spores.mL-1) and 1.8 mL of HPLC purified pigment resuspended in sterile YPD broth.

Nine phytopathogenic fungi were tested: *B. cinera* ICMP16621, *S. sclerotiorum* ICMP13844, *Alternaria alternate* ICMP1099-96, *Phomopsis viticola* ICMP5537, *Mycosphaerella graminicola* ICMP12504-95, *Rhizoctonia solani* ICMP11620, *Magnaporthe grisea* ICMP14481, *Sclerotium cepivorum* ICMP10916-91, and *Venturia inaequalis* ICMP4095-96. Three different concentrations of antifungal compound were tested: 2.7, 1.3 and 0.7 mg·mL-1 respectively. The cultures were incubated at 25° C. Each treatment was prepared in triplicate. The germinated spores were observed and recorded at 12, 24, 48, 72, 96, 120, and 240 hours. The percentage of spores germinated was determined by microscopic examination of 3 microscopic fields (haemocytometer) per sample. Spores were considered germinated when the germ tube length was equal or longer than the diameter of the spore. YPD broth without antifungal compound was used as positive control.

(k) Chemical Characterization

UV-Vis spectra were measured with a Hitachi High-Technologies Corporation spectrophotometer model U1800. IR spectra were recorded on a Thermo Electron Nicolet 8700 FT-IR spectrometer. A drop was placed on top of the diamond crystal and left to dry for 1 hour to reduce the water bands which dominated the spectrum, then 100 scans were collected at a resolution of 4 cm$^{-1}$ and averaged. The angle of incidence of the IR beam was 45° and the spectrum was ATR-corrected and baseline-corrected. Direct infusion electrospray FT-ICR MS analysis was carried out on a Thermo LTQ-FT mass spectrometer in aqueous methanol in positive ion mode. NMR spectra were recorded on a Bruker Avance 600 spectrometer equipped with a triple-resonance cryoprobe (Bruker, Karlsruhe, Germany) at 600 MHz for 1H and 150 MHz for 13C in DMSO-d6. TMS was used as an internal standard.

(l) Comparison of Different Strains of *E. purpurascens*

The *Epicoccum purpurascens* strains ICMP1732, ICMP2048, ICMP2931, ICMP10458, ICMP10459, ICMP10460, ICMP11503, ICMP13352, ICMP15700, ICMP15816 and ICMP16305 were all tested to determine whether they produced the compound of Formula (IV) produced by *Epicoccum purpurascens* strain SVB-F1. Each strain was cultured and extracellular products extracted as described above. The culture extracts were pre-purified by solid-phase extraction as described above and the purified extract were analysed by HPLC and direct infusion electrospray FT-ICR MS as above.

2. Results (a) Antagonism of Filamentous Fungi by *E. purpurascens* SVB-F1

*E. purpurascens* showed a pronounced antifungal activity when co-cultured on protein-rich agar plates with other filamentous fungi, resulting in a clear inhibition zone around *E. purpurascens* colonies (data not shown). No antimicrobial activity against yeasts, Gram positive or Gram negative bacteria was observed (data not shown).

(b) Properties and Production of the Compound of Formula (IV), Named "Epicoccaene"

*E. purpurascens* SVB-F1 when cultivated on protein-rich media actively secretes a pigmented exudate. This pigmented exudate was fractionated as described above and when tested according to the methods described above showed a pronounced antifungal activity against filamentous fungi. No antimicrobial activity was observed against yeasts, Gram positive or Gram negative bacteria (data not shown).

*E. purpurascens* SVB-F1 can grow well in minimal mineral medium with glucose and ammonium as respective sole carbon and nitrogen sources but only produced the pigmented exudate when grown on media containing proteinaceous substrates such as peptone, yeast extract, and potato extract (data not shown). Growing *E. purpurascens* SVB-F1 on minimal mineral agar medium supplemented with individual amino acids led to the production of yellow pigment when histidine was supplemented to the medium (data not shown).

The compound of Formula (IV) isolated from the pigmented exudate of *E. purpurascens* SVB-F1, hereinafter "Compound 1" is readily soluble in water and polar organic solvents such as methanol, and ethanol. It was found to be unstable under acidic conditions changing from a bright yellow colour to a pale orange. But when an acidic solution of Compound 1 was adjusted to pH 12, it recovered its bright yellow colour suggesting a reversible pH-dependent structural rearrangement. Table 1 above summarises the stability of Compound 1 to different conditions. It exhibited pronounced degradation when dissolved in solution of organic acids (10% w/w) as well as moderate light sensitivity when dissolved in water at neutral pH. However, when dissolved in water at pH 8.0 or higher, in methanol or in sugar solutions (10% w/w), its resistance to light increased (Table 1). Compound 1 also appears to be resistant to temperature and microwave radiation (Table 1), and its antioxidant power determined by FRAP (ferric reducing antioxidant power) and phosphomolybdenum assays as well as its radical scavenging ability are comparable to those of ascorbic acid (data not shown).

(c) Chemical Characterisation

Compound 1 has the molecular mass of 612 and the molecular formula of $C_{34}H_{45}O_{10}$ from ES/FT-ICR/MS (found 613.29973 for MH+, $C_{34}H_{45}O_{10}$) measurements, indicating that Compound 1 is an isomer of orevactaene, a binding inhibitor of HIV-1 Rev protein also isolated from an *E. purpurascens* culture (Shu et al, 1997). However the maximal UV absorption of the purified compound was obtained at 428 nm suggesting a slightly different conjugation system compared to orevactaene which presents UV max at 432. The IR spectrum of Compound 1 showed the strong absorption characteristics of hydroxyls (3375.5 and 3220.0 cm$^{-1}$), hydroxyls linked to carbonyls (2903.6-3023.0 cm$^{-1}$), conjugated carbonyl (1676.8 cm$^{-1}$), and additional absorptions suggestive of the presence of an ester/lactone (1093.9-1204.9 cm$^{-1}$) and alkenes (1005.1 cm$^{-1}$). NMR and $^{13}$C NMR spectra of Compound 1 were almost identical with those of orevactaene (data not shown). However, larger than average chemical shift differences were observed for C1, C2, C8 and C7, which indicate structural differences between Compound 1 and orevactaene. Based on HMBC, HSQS and COSY connectivity data, the structure of Compound 1 was determined to be Formula (IV) described above:

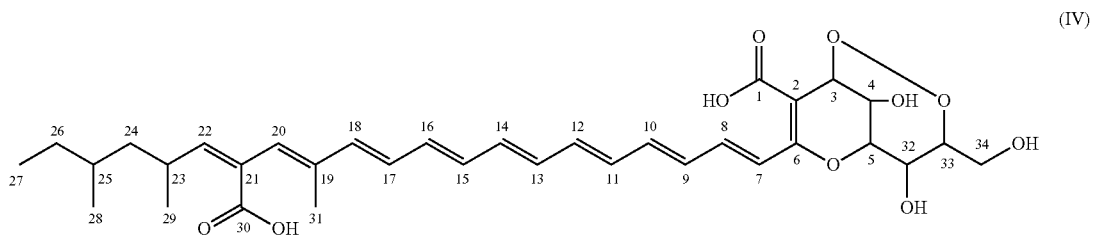 [SMILES: CCC(C)CC(C)/C=C(/C=C(C)/C=C/C=C/C=C/C=C/C=C/C=C/C1=C(C(=O)O)C2OOC(CO)C(O)C(O1)C2O)C(=O)O]

(IV)

Compound 1 possesses two major structural differences compared to orevactaene. Firstly, Compound 1 has a carboxyl group at C1, which explain the chemical shift differences of C1, C2, C8 & C7. Secondly, despite not dramatically influencing the resonance of C3 and C33, it is postulated that the oxygen bond to these carbons is linked forming a seven-membered peroxide ring because this is the only way to match the molecular mass of 612 and the corresponding fragmentation pathways determined by high-resolution mass spectrometry shown in the representation of the compound of Formula (IV) below.

two were isolated outside New Zealand (ICMP10458 ["overseas"] and ICMP13352 [United Kingdom]) and nine were isolated from different parts of New Zealand. Only two *E. purpurascens* strains, ICMP13352 and ICMP1732, failed to produce Compound 1. No pigment production was observed during growth of these strains either.

INDUSTRIAL APPLICABILITY

The compounds, isolates, compositions and methods of the invention are useful to treat or prevent fungal infections,

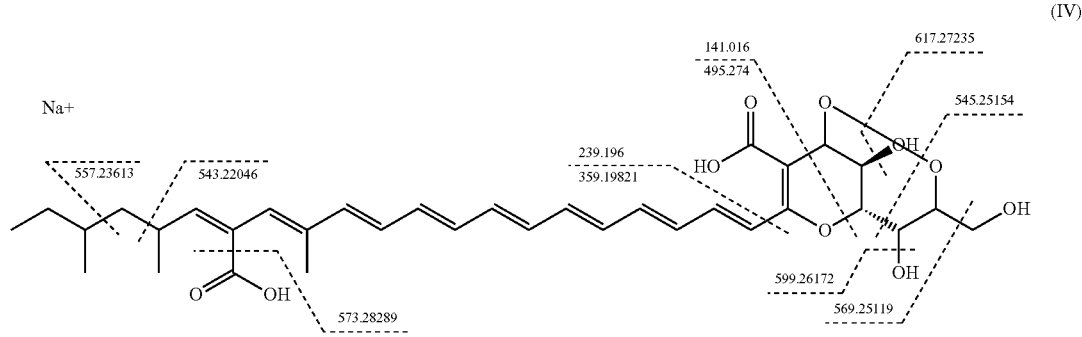 [SMILES: CCC(C)CC(C)/C=C(/C=C(C)/C=C/C=C/C=C/C=C/C=C/C=C/C1=C(C(=O)O)C2OOC(CO)C(O)[C@H](O1)[C@@H]2O)C(=O)O ; [Na+]]

(IV)

Also, eleven double bonds are present in the proposed structure for Compound 1, which is close to 12.5 predicted by high resolution MS. The stereochemistry of the chiral centres at C4, C5, C32 and C33 could not be determined unambiguously with current data. Further NMR experiments are required.

(d) Biological Activity—Inhibition of Mycelial Growth by Compound 1

Compound 1 purified by HPLC showed strong activity against *B. cinera* ICMP16621, *S. sclerotiorum* ICMP13844, and *A. supraseptata* SVB-F2, producing a distinctive zone of inhibition in the agar diffusion assays (data not shown). No antimicrobial activity against *Candida albicans* SC5614, *Candida utilis* 02/DO0981, *Saccharomyces cerevisiae* BM45, *Staphylococcus epidermis* SVB-B12, *Escherichia coli* SVB-B11 or *Pseudomonas aeruginosa* SVB-B10 was observed using agar diffusion assays (data not shown).

(e) Biological Activity—Inhibition of Spore Germination by Compound 1

Compound 1 was also able to completely inhibit spore germination of *B. cinera* during incubation in rich culture medium for 10 days (data not shown). In comparison, *B. cinera* spores were fully germinated within 12 hours of incubation in the positive control samples, which demonstrates the strong inhibition effect of Compound 1 (data not shown). All three different concentrations of Compound 1 tested were able to completely inhibit spore germination not only of *B. cinera*, but also of *S. sclerotiorum* ICMP13844, *A. alternata* ICMP1099-96, *P. viticola* ICMP5537, *R. solani* ICMP11620, *M. grisea* ICMP14481, *S. cepivorum* ICMP10916-91, and *V. inaequalis* ICMP4095-96; which indicate that the minimal inhibition dose (MID) of compound 1 against these fungi is below 0.7 mg/mL. Only *M. graminicola* ICMP12504-95 was resistant to all concentrations of Compound 1 tested.

(f) Chemical Comparison of Different Strains of *E. purpurascens*

Eleven additional *E. purpurascens* strains were subsequently obtained to determine whether they produced Compound 1. Within the eleven *E. purpurascens* strains studied, particularly filamentous fungal inventions in animals and plants, alone or delivered separately, simultaneously or sequentially with another pharmaceutically or agriculturally acceptable agent.

REFERENCES

Shu Y Z, Ye Q, Li H, Kadow K F, Hussain R A, Huang S, Gustavson D R, Lowe S E, Chang L P, Pirnik D M, Kodukula K. 1997. Orevactaene, a novel binding inhibitor of HIV-1 rev protein to rev response element (RRE) from *Epicoccum nigrum* WC47880.

Tripathi P, Dubey N K. 2004. Exploitation of natural products as an alternative strategy to control postharvest fungal rotting of fruit and vegetable. Postharvest Biol. Technol. 32: 235-245.

Verduyn C, Postma E, Scheffers W A, Dijken J. 1992. Effect of benzoic acid on metabolic fluxes in yeasts: A continuous-culture steady on regulation of respiration and alcoholic fermentation. Yeast 8: 501-517.

The invention claimed is:

1. A method of treating or reducing risk of a fungal infection in a subject in need thereof comprising administering to said subject a composition comprising an effective amount of *Epicoccum purpurascens* strain SVB-F1 on deposit at the National Measurement Institute, Australia (NMI) under accession number V10/000331 or an extract or isolate thereof, and a pharmaceutically acceptable carrier; wherein said carrier is selected from the group comprising alcohol, mineral oil and vegetable oil.

2. The method of claim 1 wherein the fungal infection comprises infection by a filamentous fungus.

3. The method of claim 2 wherein the fungus is
f. of the family Gnomoniaceae (for example, *Apiognomonia supraseptata*), Cortiaceae (for example, *Rhizoctonia solani*), Magnoporthaceae (for example, *Magnaporthe grisea*), Mycosphaerellaceae, Pleosporaceae (for example, *Alternaria alternata*), Sclerotiniaceae (for example, *Botrytis cinerea* or *Sclerotinia sclerotiorum*), Typhulaceae (for example, *Sclerotium cepivorumi*), Valsaceae (for example, *Phomopsis viticola*), or Venturiaceae (for example, *Venturia inaequalis*);

g. of the genus *Apiognomonia* (for example, *Apiognomonia supraseptata*), *Alternaria* (for example, *Alternaria alternata*), *Botrytis* (for example, *Botrytis cinerea*), *Botryotinia*, *Magnaporthe* (for example, *Magnaporthe grisea*), *Phomopsis* (for example, *Phomopsis viticola*), *Rhizoctonia* (for example, *Rhizoctonia solani*), *Sclerotinia* (for example, *Sclerotinia sclerotiorum*), *Sclerotium* (for example, *Sclerotium cepivorumi*), or Venturiaceae (for example, *Venturia inaequalis*);

h. *Apiognomonia supraseptata, Alternaria alternata, Botrytis cinerea, Botryotinia* spp., *Magnaporthe grisea, Phomopsis viticola, Rhizoctonia solani, Sclerotinia sclerotiorum, Sclerotium cepivorumi,* or *Venturia inaequalis;* i. of the family Dothioraceae (for example, *Hortaea werneckii*, syn. *Phaeoannellomyces werneckii*), Trichosporonaceae (for example, *Trichosporon beigelii*), Piedraiaceae (for example, *Piedraia hortae*), Arthrodermataceae (for example, *Trichophyton rubrum, Microsporum gypseum* or *Epidermophyton floccosum*), Sphaeropsidaceae (for example, *Scytalidium dimidiatum*, syn *Hendersonula toruloidea* or *Scytalidium hyalinum*), or Microascaceae (for example, *Scopulariopsis brevicaulis*);

j. of the genus *Hortaea* (for example, *Hortaea werneckii*, syn. *Phaeoannellomyces werneckii*), *Trichosporon* (for example, *Trichosporon beigelii, Piedraia* (for example, *Piedraia hortae*), *Trichophyton* (for example, *Trichophyton rubrum*), *Microsporum* (for example, *Microsporum gypseum*), *Epidermophyton* (for example, *Epidermophyton floccosum*), *Hendersonula* (for example, *Hendersonula toruloidea*), *Scytalidium* (for example, *Scytalidium hyalium*), or *Scopulariopsis* (for example, *Scopulariopsis brevicaulis*);

or the fungal infection is selected from anthracnose (for example, oak anthracnose), canker (for example, stem canker of tomato), ringspot disease (for example, ringspot disease of pear), blight and lesions of vegetables (for example, parsley leaf blight), fruit rot (for example, grey rot and noble rot of grapes), blast disease or bright disease (for example, rice rotten neck, rice seedling blight, blast of rice, oval leaf spot of graminea, pitting disease, ryegrass blast, and johnson spot), cane and leaf spot (for example, leaf and berry spot of grapes), damping off (for example, death of seedlings in agriculture), wire stem (for example, disease of cabbage, cauliflower and related plants), white mould (for example, white mould in soy beans and dry edible beans), wilt or stalk rot (for example, steam rot in canola), southern blight (blight of wheat and tomato), and scab lesions (for example, apple scab).

4. The method of claim 1 wherein the composition comprises a reproductively viable form and amount of *Epicoccum purpurascens* strain SVB-F1 on deposit at the National Measurement Institute, Australia (NMI) under accession number V10/000331.

5. A method of treating or reducing risk of a fungal infection and/or infestation on a target surface in need thereof comprising applying to said target surface a composition comprising an effective amount of *Epicoccum purpurascens* strain SVB-F1 on deposit at the National Measurement Institute, Australia (NMI) under accession number V10/000331 or an extract or isolate thereof, and an agriculturally or pharmaceutically acceptable carrier; wherein said carrier is selected from the group comprising alcohol, mineral oil and vegetable oil.

* * * * *